US00PP27773P3

(12) United States Plant Patent
Maillard et al.

(10) Patent No.: US PP27,773 P3
(45) Date of Patent: Mar. 14, 2017

(54) NECTARINE TREE NAMED 'NECTARNOVALA'

(50) Latin Name: ***Prunus persica* (L.) Batsch**
Varietal Denomination: NECTARNOVALA

(71) Applicant: AGRO SELECTIONS FRUITS, Elne (FR)

(72) Inventors: Arsène Maillard, Elne (FR); Laurence Maillard, Elne (FR)

(73) Assignee: AGRO SELECTIONS FRUITS, Elne (CH)

( * ) Notice: Subject to any disclaimer, the term of this patent is extended or adjusted under 35 U.S.C. 154(b) by 0 days.

(21) Appl. No.: 14/757,160

(22) Filed: Nov. 27, 2015

(65) Prior Publication Data

US 2016/0157398 P1 Jun. 2, 2016

(30) Foreign Application Priority Data

Nov. 27, 2014 (QZ) ..... PBR 2014/3176

(51) Int. Cl.
*A01H 5/08* (2006.01)

(52) U.S. Cl.
USPC ..... Plt./188

(58) Field of Classification Search
USPC ..... Plt./188
CPC ..... A01H 5/0856
See application file for complete search history.

*Primary Examiner* — Kent L Bell
(74) *Attorney, Agent, or Firm* — Westerman, Hattori, Daniels & Adrian, LLP

(57) ABSTRACT

A new and distinct variety of white nectarine tree denominated 'NECTARNOVALA' has fruits with high eating quality and very long shelf life without alteration before and after harvesting, with a semi-sweet white flesh comprising a red pigmentation, and an attractive luminous and homogenous skin with a high percentage of purple red blush on skin surface.

2 Drawing Sheets

Botanical classification: *Prunus persica* (L.) Batsch.

Variety denomination: 'NECTARNOVALA'.

This application claims priority of Community plant variety right No. 2014/3176 filed on Nov. 27, 2014 which is hereby incorporated by reference in its entirety.

BACKGROUND OF THE NEW VARIETY

The present invention relates to a new and distinct variety of white nectarine tree, *Prunus persica* (L.) Batsch, which has been given the variety denomination 'NECTARNOVALA'. This new tree produces fruits with a long shelf life without alteration both on the tree after growth completion and after harvesting, very good eating quality, clingstone white flesh fruits with red pigmentation for fresh market in July in the Pyrénées-Orientales department, France. Contrast is made to 'NECTARBOOM' white nectarine tree (U.S. Plant Pat. No. 23,355) for reliable description. 'NECTARNOVALA' is a promising candidate for commercial success in that it has very attractive fruits with very long shelf life without alteration both before and after harvesting.

ORIGIN OF THE VARIETY

The 'NECTARNOVALA' white nectarine tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'NECTARNOVALA' variety resulted from a pollinated cross between the 'NECTAVISTA' (U.S. Plant Pat. No. 21,139) yellow nectarine tree, which was used as the seed parent, and the 'NECTARFLORA' (U.S. Plant Pat. No. 22,504) white nectarine tree which was used as the pollen parent.

The 'NECTARNOVALA' variety was obtained by hybridizing and propagated by grafting on a "INRA GF677" rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'NECTARNOVALA' white nectarine tree blooms at the end of February or early in March near Elne in the Pyrénées-Orientales department, France. More particularly, it blooms between February 18$^{th}$ and March 16$^{th}$. The blooming period is considered early. However, it was observed that its early date of blooming seems to be highly dependant on climatic conditions.

The first fruit of 'NECTARNOVALA' ripens generally at the end of June or during the first two weeks of July, approximately 5 to 7 day after the ripening of the first fruit of 'NECTARBOOM' white nectarine tree (U.S. Plant Pat. No. 23,355). More particularly, it usually ripens between June 22$^{nd}$ and July 18$^{th}$. Thus, the time of maturity of fruits for consumption is considered early. However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
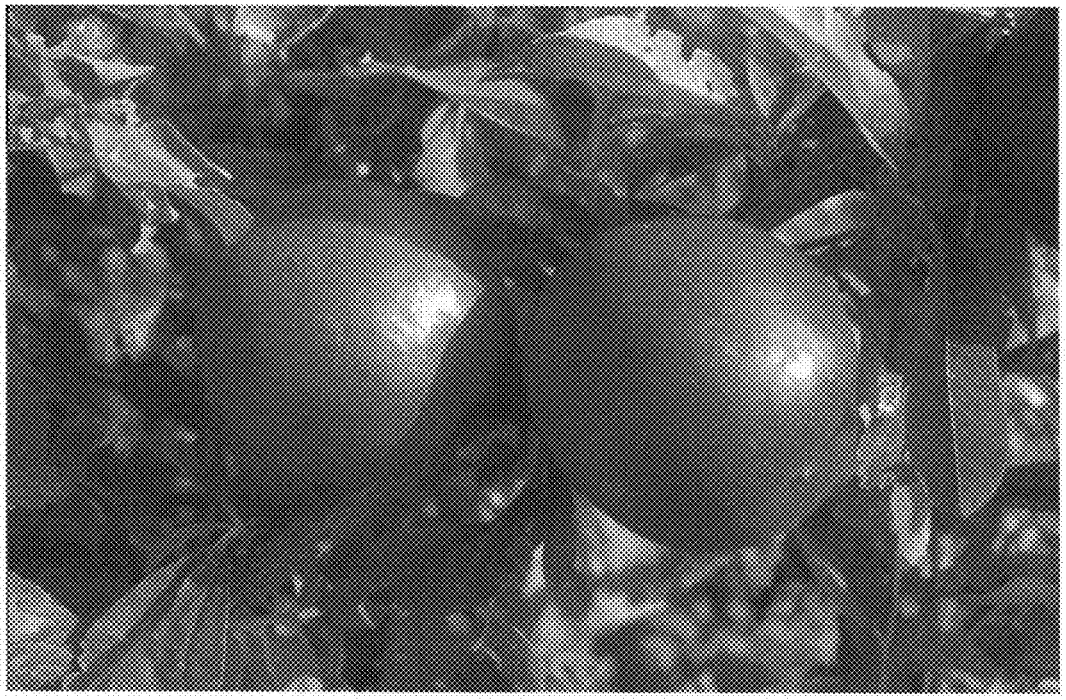
FIG. 1 is a color photograph showing a branch of a tree of the new variety in orchard, bearing fruits.
Figure 2:
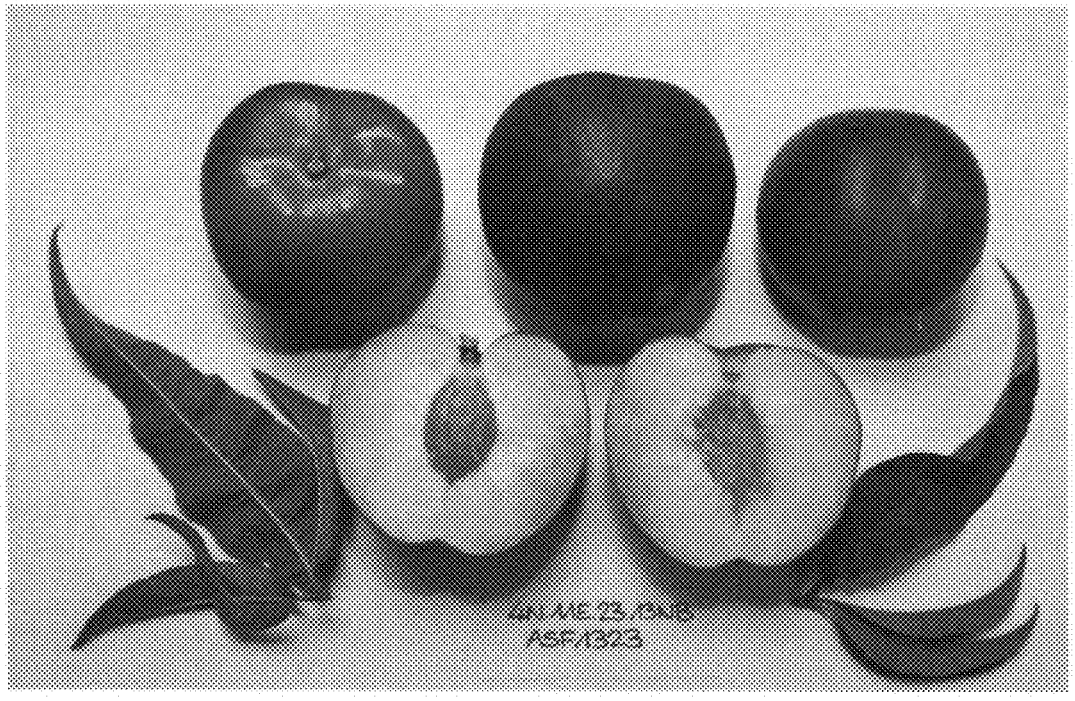
FIG. 2 is a color photograph which shows four typical specimens of the fruit, one having been cut in half with the pit being left into the half for depicting fruit flesh and pit of the new variety.
Figure 3:
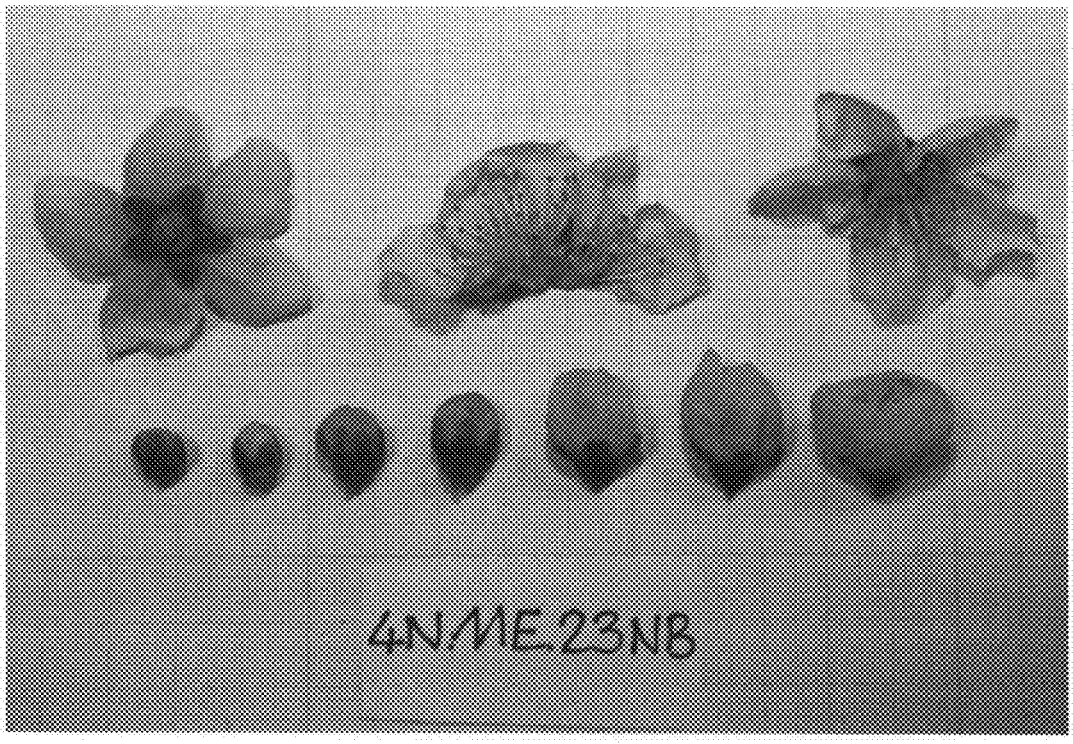
FIG. 3 is a color photograph which depicts the flower buds at different development stages, and the reverse and side view of the flower and the reproductive organs with petals removed, of the new variety.
Figure 4:
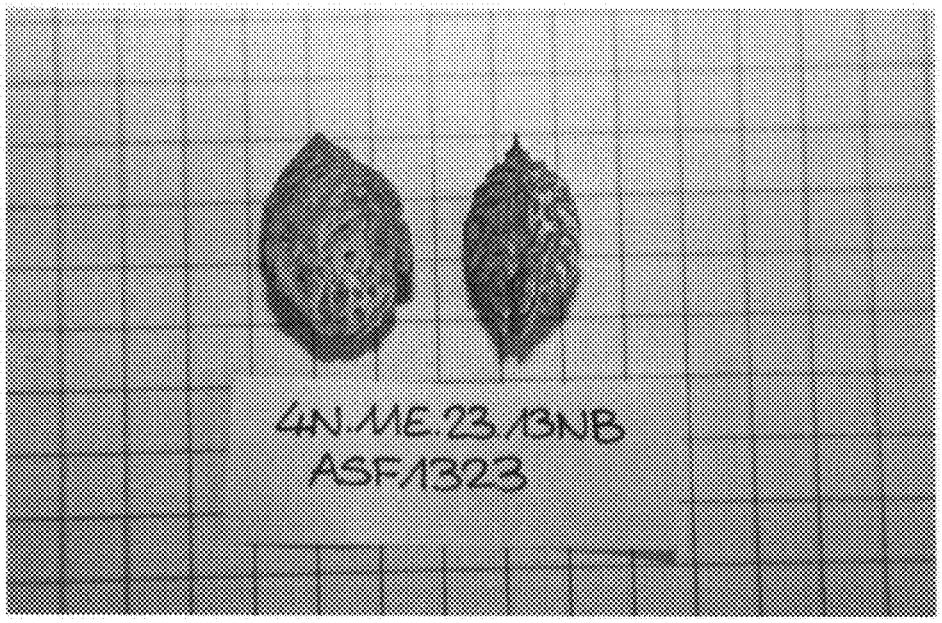
FIG. 4 is a color photograph that shows different views of the stone of the new variety 'NECTARNOVALA'.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'NECTARNOVALA' is high, due to fruit very long shelf life without alteration after harvesting.

Trees are medium vigorous and large stature half-standing in a semi-flared to semi-upright out aspect. The anthocyanic coloration of flowering shoot is present excluding brushwood side away from sun. The time of beginning of flowering is considered early; flowering begins at the end of February. The type of flower is showy (rosette) with medium petal size. Petals are pale pink. Leaf glands are present and reniform. The fruit flesh is white generally with a red pigmentation. The fruit skin is very thick, with a red purple blush on a red orange background. The stone is clingstone and the size is medium to large. Fruit taste is semi-sweet, very aromatic and with a high level of sugars.

Compared to 'NECTARBOOM' white nectarine tree (U.S. Plant Pat. No. 23,355), 'NECTARNOVALA' ripens approximately 5 to 7 days after. Moreover, the flowers of 'NECTARNOVALA' are showy type (rosette) whereas 'NECTARBOOM' variety has a non-showy type of flowers (campanulate). 'NECTARNOVALA' variety produces a higher quantity of both flowers and fruits than 'NECTARBOOM' variety.

Compared to its female parent 'NECTAVISTA' (U.S. Plant Pat. No. 21,139), which is a yellow nectarine tree, the new variety 'NECTARNOVALA' is a white nectarine tree. The fruits of 'NECTARNOVALA' are bigger in size (homogenous 2A) in comparison with the fruits of 'NECTAVISTA' (homogenous AA-A).

Compared to its male parent 'NECTARFLORA' (U.S. Plant Pat. No. 22,504), which has round leaf glands, the leaf glands of the new variety 'NECTARNOVALA' are reniform. The bloom quantity for the variety 'NECTARFLORA', more than 45 flowers per meter, is higher than the bloom quantity for 'NECTARNOVALA', which is typically between 35 and 40 flowers per meter. Moreover, the 'NECTARFLORA' variety is considered to have a semi-low chilling requirement whereas the new variety 'NECTARNOVALA' has a medium to high chilling requirement.

DETAILED DESCRIPTION

Referring more specifically to the pomological details of this new and distinct variety of white nectarine tree, the following was observed on trees in their third and fourth growing seasons (second and third years of production) for trees, fruits, leaves and stones and in their third growing season (second year of production) for flowers under the ecological conditions prevailing at the orchards located near the town of Elne, Pyrénées-Orientales departement, France. All observations have been done on rootstock cultivars. Used rootstocks were "INRA GF677" trees. All major color code designations are by reference to The R.H.S. Colour Chart (Fourth Edition) provided by The Royal Horticultural Society of Great Britain.

Tree:

*Size*.—Generally. — Considered large. The tree size the first year was approximately 250 cm. The tree was pruned during each following dormant season to a height of approximately 250 cm. Current season shoots growth could reach 60 to 80 cm. The tree size from the second year (second and next years) reached a final height of 310 to 330 cm including current season shoots length. The tree size is consistently reduced to 250 cm the next years.

*Spread*.—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor*.—Considered medium vigorous.

*Productivity*.—Very Productive and regular, every year. Fruit set is spaced by thinning to develop the remaining fruit into the desired market sized fruit. The number of the fruit set varies with the prevailing climatic conditions and cultural practices employed during the bloom period, and is therefore not distinctive of the present variety.

*Bearer*.—Very regular. The fruit distribution is considered homogenous on mixed branches and spurs having more than 1 year. Thinning of 1 fruit out of 3 was necessary for the tree valorisation. Thinning was necessary every year during the years of observation.

*Form*.—The 'NECTARNOVALA' variety has naturally a semi-flared to semi-upright shape.

*Density*.—Considered dense.

*Hardiness*.—The present tree was grown and evaluated in France. The variety appears to be hardy under the central Pyrénées-Orientales departement typical climatic conditions. Experimentations on different sites with winter chilling requirement comprised between 350 hours and 1200 hours showed a good behaviour of the tree in all cases. No damages were caused by ascertained temperatures as low as −12 degrees Celsius in winter. The tree was also very resistant to frosty springtime weather.

Trunk:

*Diameter*.—Between 6.5 and 7.5 centimeters in diameter when measured at a distance of approximately 30 centimeters above the soil level.

*Bark texture*.—Considered smooth to rough, with lenticels.

*Lenticels*.—Numerous lenticels are present. The number of lenticels reaches 3 or 4 lenticels per $cm^2$. The lenticels range in size from approximately 4.0 millimeters to 6.0 millimeters in width, and approximately 2.0 millimeters in height.

*Lenticel color*.—The outside of lenticels has a silver-grey color (RHS Grey 201 C), whereas the inside is considered brown (RHS Greyed Orange 167 A to RHS Greyed Orange 167 B).

*Bark coloration*.—The bark has a silver-grey color (RHS Grey 201 A to RHS Grey 201 B) slightly darker than the outside of lenticels color.

Branches:

*Size*.—Mature branches and current season shoots are considered medium for the variety.

*Diameter*.—Average as compared to other nectarine varieties. The current season shoots have a diameter from 5.0 to 7.0 millimeters, and branches of the second year have a diameter from 11.0 to 15.0 millimeters.

*Surface texture*.—Average, wood which is several years old has no furrowed appearance. A few furrows appear on the trunk.

*Crotch angles*.—Primary branches are considered variable, but the crotch angles are generally between 40 degrees and 60 degrees from the horizontal axis. This particular characteristic is not considered distinctive of the variety, however.

*Current season shoots*.—Internode length: Generally between 25.0 and 30.0 millimeters. Color of mature branches: Medium brown (RHS Grey Brown 199 A).

*Current seasons shoots*.—Color. — The color of new shoot tips is considered a pale yellow-green (RHS Yellow Green N144 A) on lower part of new shoot tips, whereas the upper part is darker and colored in brown-purple (RHS Greyed Purple 183 A).

Leaves:

*Size*.—Considered medium for the species. The ratio leaf length/leaf width is 3.62.

*Leaf length*.—Approximately 117.0 to 153.0 millimeters with leaf petiole. The medium length is 141.0 millimeters.

*Leaf width*.—Approximately 34.0 to 43.0 millimeters. The medium width is 39.0 millimeters.

*Leaf base shape*.—Concave.

*Leaf form*.—Lanceolate.

*Leaf tip form*.—Acuminate.

*Leaf color*.—Upper leaf surface. — Dark Green (RHS Green 147 A). Lower surface. — A lighter green (RHS Green 146 A to RHS Green 146 B) than the upper leaf surface color.

*Leaf texture*.—Smooth and glabrous.

*Leaf venation*.—Pinnately veined.

*Mid-vein*.—Color. — Light green, almost yellow (RHS Yellow Green 150 D). The color may evolve with maturity.

*Leaf margins*.—Slightly undulating.

*Form*.—Considered slightly dentate.

*Uniformity*.—Leaves are isolated or grouped by 2 or 3. In this last case, one leaf of normal size is found with one or two smaller leaves (at least 50% smaller).

*Leaf petioles*.—Size. — Considered medium. Length. — About 10.0 to about 13.0 millimeters. Diameter. — About 1.5 to 2.0 millimeters.

*Petioles color*.—Upper petiole surface. — Light green (RHS Yellow Green 144 A to RHS Yellow Green 144 B). Lower surface. — Light green (RHS Yellow Green 144C).

*Leaf glands*.—Size. — Considered medium. Their length is about 1.2 millimeters and their width is about 1.0 millimeter. Number. — Generally 2 or 3 glands per leaf. Type. — Reniform. Color. — On young leaves, leaf glands color is considered a light green (RHS Yellow Green 144 B to RHS Yellow Green 144 A). On older leaves, leaf glands color turns to a dark brown (RHS Grey Brown 199 A to RHS Grey Brown 199 B). Margins. — Smooth and regular.

*Leaf stipules*.—Generally. — No leaf stipules were observed. But as seen in the characteristic relative to the leaves uniformity, it is possible to find leaves by groups of 2 or 3, with a normal-size leaf and smaller ones.

Flowers:

*Flower buds*.—Generally. — At pre-floral stage of development, the floral buds are conic in form with a round tip. Their form is evolving until blooming, with variables dimensions. Just before blooming, floral buds are approximately 12.0 millimeters wide and approximately 20.0 millimeters long. Color. — This characteristic is dependent upon the proximity to bloom. At pre-floral stage (stage A) of development, the bottom of the flowers buds, formed by the sepals, is of purple-brown color (RHS Greyed Purple 183 A or RHS Greyed Purple 183 B or RHS Greyed Purple 183 C or RHS Greyed Purple 187 B and RHS Grey Brown Group 199 A at the base). The corolla, formed by the petals, is generally of medium pink color (RHS Red Purple 65 B). Petals color shows an evolution until the end of flowering.

*Hardiness*.—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom*.—The blooming time generally begins at the end of February. The bloom was observed on 2014 between February $28^{th}$ and March $2^{nd}$.

*Blooming time*.—Considered early-season in relative comparison to other commercial nectarine cultivars grown in the Pyrénées-Orientales departement, France. The date of full bloom is observed at the middle of the blooming period. The date of bloom varies slightly with climatic conditions and cultural practices. Thus the first full bloom was observed on 2013, from February 20$^{th}$ until February 28$^{th}$ and then from Feb. 28 until Mar. 2, 2014 and from Mar. 3 until Mar. 16, 2015.

*Duration of bloom*.—Approximately 13 days. This characteristic varies slightly with the prevailing climatic conditions.

*Flower type*.—The variety is considered to have a showy type flower (rosette type).

*Flower size*.—Considered medium to large. Flower diameter at full bloom is approximately 38.0 to 42.0 millimeters.

*Bloom quantity*.—Considered abundant, approximately between 35 and 40 flowers per meter, with a good distribution and a high rate of fruit set.

*Flower bud frequency*.—Generally 2 flower buds appear per node, occasionally 1.

*Petal size*.—Generally. — Considered medium to large.

*Length*.—Generally between 20.0 and 22.0 millimeters.

*Width*.—Generally between 19.0 and 21.0 millimeters.

*Petal form*.—Round-shaped.

*Petal count*.—Generally 5.

*Petal texture*.—Smooth, soft and glabrous.

*Petal color*.—Both surfaces of the petal are colored with a medium pink (RHS Red Purple 65 B to RHS Red Purple 65 D) when young, becoming slightly darker until the end of blooming.

*Fragrance*.—Sweet.

*Petal claw*.—Form. — The claw is considered to have a conic form, with a slightly curved tip. Length. — Approximately 1.5 millimeters. Width. — Approximately 1.0 millimeters. Color. — The color of petal claw is darker than the petal color (RHS Red Purple 61 B).

*Petal margins*.—Slightly undulating.

*Petal apex*.—Generally. — The petal apices are generally wide dome-shaped.

*Flower pedicel*.—Length. — Considered medium to large and having an average length of approximately 2.0 millimeters. Diameter. — Considered average, approximately 1.5 millimeters. Color. — Green (RHS Yellow Green N144 A to RHS Yellow Green N144 B).

*Calyx*.—Internal surface texture. — Smooth and glabrous. Color. — At the stage F of blooming, when the flower is open, the inner surface of the calyx is greenish yellow (RHS Yellow Group 13A to RHS Yellow Group 13B or Yellow Orange Group 17A or RHS Yellow Green 150 A to RHS Yellow Green 150 B). The outer surface of the calyx is considered of purple-brown color (RHS Greyed Purple 183 A or RHS Greyed Purple 183 B or RHS Greyed Purple 183 C or RHS Grey Purple 187 B and RHS Yellow Green 144 A to B at the base).

*Sepals*.—Number. — Generally five sepals. Surface texture. — The outer surface has a short, fine pubescent texture. Margins. — Smooth. Form. — Conic with a round tip. Size. — Average. Length. — Approximately 5.0 to 6.0 millimeters. Width. — Approximately 4.0 to 5.0 millimeters. Color. — At the stage F of blooming, the inner surface of the sepals is greenish yellow (RHS Yellow Group 13A to RHS Yellow Group 13B or Yellow Orange Group 17A or RHS Yellow Green 150 A to RHS Yellow Green 150 B). The outer surface of the sepals is considered of purple-brown color (RHS Greyed Purple 183 A or RHS Greyed Purple 183 B or RHS Greyed Purple 183 C or RHS Grey Purple 187 B and RHS Yellow Green 144 A to B at the base).

*Average number of stamens per flower*.—Approximately 38 to 42 stamens per flower.

*Anthers*.—Generally. — Small to medium in length. Color. — At the beginning of maturity, anthers show an orange yellow color (RHS Yellow Orange 16 A to RHS Yellow Orange B) or red to red orange color (RHS Red Group N34 A or RHS Greyed Red Group 178 A). The color may evolve with maturity to turn in a red orange color. Pollen production: Pollen is abundant, and has an orange yellow color (Approximately RHS Yellow Orange 17 B to RHS Yellow Orange 17C) which may evolve with maturity. The present variety is considered auto-fertile (self-pollinating).

*Filaments*.—Size. — Medium length, between 10.0 and 15.0 millimeters in length. Filaments length is generally higher to the pistil's length.

*Color*.—Considered light pink (approximately RHS Red Purple 62 C to RHS Red Purple 62 D or RHS Red Purple 73 A to RHS Red Purple 73 B). The color becomes darker during the blooming.

*Pistil*.—Number. — Usually 1. Generally. — Average in size. Length. — Approximately 15.0 to 18.0 millimeters including the ovary. Generally equal to stamen length, if not slightly smaller. Color. — Considered a very pale green (RHS Yellow Green Group 151 D) at the beginning of flowering, it becomes lighter and lighter (RHS Yellow Green 150 D) during the blooming and sometimes very slightly pinky (RHS Red Group 36D) at the end of the blooming. Surface texture. — Glabrous.

Fruit:

*Maturity when described*.—Very firm in ripe conditions (shipping ripe).

*Date of first picking*.—Jul. 10, 2013.

*Date of last picking*.—The date of harvest varies slightly with the prevailing climatic conditions. The 'NECTARNOVALA' variety has an early date of picking, and a grouped maturity. The maturity is grouped within 9 days and the harvest is generally performed in two runs. Last known picking times carry on from Jul. 10 to Jul. 18, 2013, then from Jun. 23 to Jul. 1, 2014 and from Jun. 24 to Jul. 2, 2015.

*Size*.—Generally. — Homogeneous in size. Generally main size 2A.

*Average cheek diameter*.—Approximately 68.0 to 76.0 millimeters.

*Average axial diameter*.—Approximately 63.0 to 71.0 millimeters.

*Typical weight*.—Generally about 180.0 to 230.0 grams. This characteristic is high dependent upon the prevailing cultural practices, and therefore is not particularly distinctive of the variety.

*Fruit form*.—Generally. — Round to slightly oblong. The fruit is generally uniform in symmetry, viewed from the suture's plane. Fruit suture: Wide-mouthed and slightly marked, extending from the base to the apex. No apparent callousing or stitching exists along the suture line. Not pointed.

*Suture*.—Color. — The suture has generally a similar color to the whole fruit color, a luminous purple red (RHS Greyed Purple 187 A).

*Ventral surface*.—Form. — Smooth.

*Apex*.—Non-prominent, generally slightly depressed.

*Base*.—Semi-flared, shallow.

*Stem cavity*.—Average depth of the stem cavity is about 10.0 to 13.0 millimeters. Average width is about 16.0 to 19.0 millimeters.

*Fruit skin*.—Thickness. — Considered very thick and strong, and the adherence of skin to flesh is strong to medium, depending on the fruit maturity. Texture. — Glabrous. Taste. — Semi-sweet, aromatic, with a high level of sugars. Tendency to crack. — None observed.

*Color*.—Blush color. — This blush color is a luminous and homogenous purple red (RHS Greyed Purple 187 A). The red blush covers 80% to 95% of the fruit skin surface on an orange red background (RHS Orange Red N34 A). The percentage of the blush on the fruit skin surface can vary, and is generally dependant upon the prevailing conditions under which the fruit was grown. Ground color. — The ground color covers approximately 5 to 20% of the fruit skin surface, and is considered orange red (RHS Orange Red N 34 A).

*Fruit stem*.—Medium in length, approximately 9.0 millimeters.

*Diameter*.—Approximately 4.0 to 5.0 millimeters.

*Color*.—Pale green (RHS Yellow Green 145 A).

*Flesh*.—Ripens. — Very homogenously, slowly. The flesh has a long shelf life. Texture. — Very firm, very dense, crunchy, melting, juicy at harvest maturity stage. Fibers. — Not fibrous. Aroma. — Pronounced. Eating quality. — Considered very good and aromatic. Flavor. — Considered semi-sweet and very aromatic. The Brix is generally superior to 13 and acidity comprised between 6 and 9 meq/100 ml. Juice. — Very juicy at complete maturity. Brix. — Generally 14.0 to 18.0 degrees. This characteristic varies slightly with the number of fruit per tree; prevailing cultural practices; and the surrounding climatic conditions. Flesh color. — White flesh (RHS White 155 B) usually with a red pigmentation (RHS Red 47 A).

Stone:

*Type*.—Clingstone, more or less adherent depending on the fruit maturity.

*Size*.—Considered medium to large for the variety. The stone size varies significantly depending upon the tree vigor, crop load and prevailing growing conditions.

*Length*.—Approximately 33.0 millimeters.

*Width*.—Approximately 24.0 millimeters.

*Diameter*.—Approximately 20.0 millimeters.

*Form*.—Elliptic.

*Base*.—Straight.

*Apex*.—Shape. — The stone apex is short, pointed. Stone Cavity: Considered medium to large size, with an ovate-form and dimensions corresponding to the stone's dimensions. Stone surface: Surface texture. — The pit is transversely furrowed on its entire surface. Furrows are more pronounced toward the apex. The stone is pitted toward the base. Relief is prominent generally and present basally. Ridges. — The surface texture is generally characterized by more prominent ridges along the ventral edges and is more prominent at the apical tip.

*Ventral edge*.—Width. — Considered small to medium, and having a dimension of approximately 2.0 millimeters at mid-suture.

*Dorsal edge*.—Shape. — Grooved. Stone color: The color of the dry stone is generally considered light orange brown (RHS Greyed Orange 164 C).

*Tendency to split*.—Splitting is very low or absent, depending on climatic conditions between blooming period and stone hardening.

*Kernel*.—Size. — The kernel is considered medium. Length. — Approximately 17.0 millimeters. Width. — Approximately 9.0 millimeters. Thickness. — Approximately 5.0 millimeters. Form. — Considered oblate and elliptic. Pellicle. — The pellicle of the kernel has a short pubescence. Color. — The kernel skin is a orange-brown (RHS Greyed Orange N167 A or RHS Greyed Orange N167 B). The almond, which is the seed of the kernel, is orange white (RHS Orange White 159 D) and has a bitter tasting. The kernel and its embryo are mature at the time of fruit maturity.

*Use*.—The subject variety 'NECTARNOVALA' is considered to be a nectarine tree of the early season of maturity, and which produces fruits that are considered firm, attractively colored with a very luminous purple red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.

*Keeping quality*.—Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degree Celsius.

*Shipping quality*.—Considered very good. The fruit of the new white nectarine variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.

*Resistance to insects and disease*.—No particular susceptibilities were noted. The present variety is not very sensitive to powdery mildew, or conservation diseases and decay due to its thick and strong skin. Although the new variety of nectarine tree possesses the described characteristics when grown under the ecological conditions prevailing near Elne, Pyrénées-Orienteles departement, France, it should be understood that variations of the usual magnitude and characteristics incident to changes in growing conditions, fertilization, pruning, pest control and horticultural management are to be expected.

We claim:

1. A new and distinct variety of white nectarine tree as illustrated and described, characterized by fruits with high eating quality and very long shelf life without alteration before and after harvesting, with a semi-sweet white flesh comprising a red pigmentation, and an attractive luminous and homogenous skin with a high percentage of purple red blush on skin surface.

* * * * *